United States Patent [19]
Ensoli et al.

[11] Patent Number: 5,990,088
[45] Date of Patent: Nov. 23, 1999

[54] METHOD FOR TREATING KAPOSI'S SARCOMA WITH ANTISENSE OLIGONUCLEOTIDES

[75] Inventors: Barbara Ensoli, Silver Spring; Robert C. Gallo, Bethesda, both of Md.

[73] Assignee: The United States of America as represented by the Department of Health and Human Services, Washington, D.C.

[21] Appl. No.: 08/463,978

[22] Filed: Jun. 5, 1995

Related U.S. Application Data

[62] Division of application No. 08/072,575, Jun. 4, 1993, abandoned.

[51] Int. Cl.$^6$ .......................... A61K 31/70; C07H 21/04; C12N 5/08
[52] U.S. Cl. ............................ 514/44; 435/366; 536/24.5
[58] Field of Search .................................. 435/91.1, 366; 514/44; 536/22.1, 24.5

[56] References Cited

U.S. PATENT DOCUMENTS 5,585,479  12/1996  Hoke et al. ............................. 536/24.5

FOREIGN PATENT DOCUMENTS 9221380  12/1992  WIPO.

OTHER PUBLICATIONS

Morrison (1991) Suppression of basic fibroblast growth factor expression by antisense oligodeoxynucleotides inhibits the growth of transformed human astrocytes. J. Biol. Chem. 266:728–734, Jan. 1991.

Rojanasakul (1996) Antisense oligonucleotide therapeutics: drug delivery and targeting. Adv. Drug Delivery Rev. 18:115–131, 1996.

New England Journal of Medicine (1982); vol. 306, No. 4, pp. 248–252.

Abraham et al., *Science*, "Nucleotide Sequence of a Bovine Clone Enclding the Angiogenic Protein, Basic Fibroblast Growth Factor", 233: 545–548.

Agarwal et al., *Nucleic Acids Research* (1979), vol. 6, No. 4, pp. 3009–3025.

Albini et al., *Cancer Research* (1987); "A Rapid in Vitro Assay for Quantitating the Invasive Potential of Tumor Cells"; 47: 3239–3245.

Barillari et al., *Journal of Immunology* (1992); "Effects of Cytokines from Activated Immune Cells on Vascular Cell Growth and HIV–1 Gene Expression"; vol. 149, No. 11, pp. 3727–3734.

Bayever et al., *Antisense Research and Development;* "Guest Editorial: Systemic Human Antisense Therapy Begins"; 2:109–110 (1992).

Becker et al., *EMBO Journal;* "Proliferation of Human Malignant Melanomas is Inhibited by Antisense Oligodeoxynucleotides Targeted Against Basic Fibroblast Growth Factor"; vol. 8, No. 12, pp. 3685–3691 (1989).

Burgess et al., *Annu. Rev. Biochem;* The Heparin–Binding (Fibroblast) Growth Factor Family of Proteins; 58:575–606 (1989).

Dagle et al., *Nucleic Acids Research;* "Targeted Degradation of mRNA in Xenopus Oocytes and Embryos Directed by Modified Oligonucleotides: Studies of An2 and Cyclin in Embryogenesis"; vol. 18, No. 16.

Ensoli et al., *Science;* "AIDS—Kaposi's Sarcoma–Derived Cells Express Cytokines with Autocrine and Paracrine Growth Effects"; 243:223–226.

Ensoli et al., *Hematol. Oncol. Clin. No. Am.;* "Pathogenesis of AIDS–Associated Kaposi's Sarcoma": 5:281 (1991).

Ensoli et al., *Immunol. Rev.;* "Cytokines and Growth Factors in the Pathogenesis of AIDS–Associated Kaposi's Sarcoma"; 127:147–155.

Ensoli et al., *Journal of Virology;* "Release, Uptake, and Effects of Extracellular Human Immunodeficiency Virus Type 1 Tat Protein on Cell Growth and Viral Transactivation", 67:277–287.

Folkman et al., *Nature;* "Angiogenesis in vitro"; 288:551–556.

Folkman et al., *Science;* "Angiogenic Factors"; 235:442–447.

Friedman–Kein, *Am. Acad. Dermatology;* "Disseminated Kaposi's Sarcoma Syndrome in Young Homosexual Men"; 5:468–471.

Gottlieb et al., *Human Pathology;* "Kaposi's Sarcoma: An Extensively Disseminated Form in Young Homosexual Men"; 13:882–892.

Haverkos et al., *N. Eng. J. Med.;* 312:1518 (1995).

Ingber et al., *Nature;* "Synthetic Analogues of Fumagillin that Inhibit Angiogenesis and Suppress Tumour Growth"; 348:555–557.

Inoue et al., *FEBS Letters;* "Sequence–Dependent Hydrolysis of RNA Using Modified Oligonucleotide Splints and RNase H"; 215:327–330 (1987).

LaPlance et al., *Nuc. Acids Res.;* "Phosphorothioate–Modified Oligodeoxyribonucleotides"; 14:9081–9093.

Loke et al., *Proc. Natl. Acad. Sci. USA;* "Characterization of Oligonucleotide Transport into Living Cells"; 86:3474–3478.

Inoue et al., *Nucleic Acids Research;* "Synthesis and Hybridization Studies on Two Complementary Nona (2'–O–methyl) Ribonucleotides"; 15:6131.

McNutt et al., *Am. J. Pathol.;* "Early Lesions of Kaposi's Sarcoma in Homosexual Men"; 111:62–77.

(List continued on next page.)

*Primary Examiner*—Nancy Degen
*Assistant Examiner*—Robert Schwartzman
*Attorney, Agent, or Firm*—Knobbe, Martens, Olson & Bear, LLP

[57] ABSTRACT

The present invention relates to a method to treat Kaposi's sarcoma (KS), and particularly, human immunodeficiency virus associated KS through the administration of antisense oligonucleotides complementary to basic fibroblast growth factor RNA.

7 Claims, 5 Drawing Sheets

OTHER PUBLICATIONS

Miles et al., *Proc. Natl. Acad. Sci. USA;* "AIDS Kaposi Sarcoma–Derived Cells Produce and Respond to Interleukin 6"; 87:4068–4072.

Roth et al., Oncogene; "Depletion of PDGF from Serum Inhibits Growth of AIDS–Related and Sporadic Kaposi's Sarcoma Cells in Culture"; 4:483.

Safai et al., *Annals of Internal Medicine;* "The Natural History of Kaposi's Sarcoma in the Acquired Immunodeficiency Sydrome" 103:744–750.

Salahuddin et al., *Science;* "Angiogenic Properties of Kaposi's Sarcoma–Derived Cells After Long–Term Culture in Vitro"; 242:430–433.

Sarin et al., *Proc. Natl. Acad. Sci. USA,* "Inhibition of Acquired Immunodeficiency Syndrome Virus by Oligodeoxynucleoside Methylphosphonates"; 85:7448–7451.

Shakin et al., *J. Biol. Chem.;* "Destablization of Messenger RNA/Complementary DNA Duplexes by the Elongatng 80 S Ribonsome"; 261:10618.

Stec et al., *J. Am. Chem. Soc.;* "Automated Solid–Phase Synthesis, Separation, and Stereochemistry of Phosphorothioate Analogues of Oligodeoxyribonucleotides"; 106:6077–6079.

Sturzl et al., *Proc. Natl. Acad. Sci. USA;* "Expression of Platelet–Derived Growth Factor and its Receptor in AIDS–Related Kaposi Sarcoma in Vivo Suggests Paracrine and Autocrine Mechanisms of Tumor Maintenance"; 89:7046.

Thompson et al., *Cancer Res.;* "Supernatants of Acquired Immunodeficiency Syndrome–Related Kaposi's Sarcoma Cells Induce Endothelial Cell Chemotaxis and Invasiveness"; 51:2670–2676.

Thompson et al., *Science;* "Site–Directed Neovessel Formation in Vivo"; 241:1349–1352.

Uhlmann et al., *Chemical Review;* "Antisense Oligonucleotides; A New Therapeutic Principle"; 90:543–584.

Weindel et al., *Biochemical and Biophysical Research Communications;* "AIDS–Associated Kaposi's Sarcoma Cells in Culture Express Vascular Endothelial Growth Factor"; 183:1167–1174.

Xerri et al., *Am. J. Pathol.;* "Fibroblast Growth Factor Gene Expression in AIDS—Kaposi's Sarcoma Detected by In Situ Hybridization"; 138:9–15.

Morrison, Suppression of Basic Fibroblast Growth Factor Expression by Antisense Oligodeoxynucleotides Inhibits the Growth of Transformed Human Astrocytes, *The Journal of Biological Chemistry,* 266:728–734, 1991.

METHOD FOR TREATING KAPOSI'S SARCOMA WITH ANTISENSE OLIGONUCLEOTIDES

This application is a divisional of application Ser. No. 08/072,575, filed Jun. 4, 1993, abandoned.

BACKGROUND OF THE INVENTION

1. Field of the Invention

The present invention relates to a method for treating Kaposi's sarcoma (KS), and particularly, treatments of human immunodeficiency virus-associated KS through the administration of antisense oligonucleotides complementary to basic fibroblast growth factor RNA.

2. Background of the Art

Kaposi's sarcoma (KS) is a proliferative disease of vascular origin frequently associated with Human Immunodeficiency Virus-1 (HIV-1) infection. CDC Task Force on KS and Opportunistic Infections, *N. Engl. J. Med.* 306:248 (1982); Safai et al *Ann. Int. Med.* 103:744 (1985); Havercos et al. *N. Engl. J. Med* 312:1518 (1985). Kaposi's sarcoma will be referred to herein as "KS", whereas HIV-1 associated Kaposi's sarcoma will be referred to herein as "AIDS-KS".

KS typically occurs as lesions in the skin, although, in most AIDS-KS patients, visceral lesions are also present. KS often arises as multiple disseminated skin lesions that in early stages resemble benign capillary hemangiomas or vascularized chronic inflammatory foci. Repeated biopsies show a progressive sarcomatous-like appearance. In more advanced stages, the lesions appear as multiple purplish to brown subcutaneous plaques or nodules, often with a verrucose surface. The characteristic histological features of KS include the proliferation of spindle-shaped cells (KS cells, considered the tumor element) and of endothelial cells, either as cellular sheets or forming new blood vessels (angiogenesis) often abnormal (slit-like spaces) containing red blood cells (CDC Task Force *N. Engl. J. Med.* 306:248 (1982); Safai et al *Ann. Int. Med.* 103:744 (1985); Havercos et al. *N. Engl. J. Med* 312:1518 (1985); Friedman-Kien, *J. Am. Acad. Dermathol.* 5:468 (1981); Gottlieb et al. *Hum. Pathol.* 13:882 (1982); Macnutt et al. *Am. J. Pathol.* 111:62 (1983)). Other KS histological features are extravascular hemorrhage with hemosiderin deposition, anaplastic fibroblast-like proliferation, and a granulation-like inflammatory reaction. Robbins et al. "Basic Pathology" p. 286 (W. B. Saunders Co., 2d ed. 1976).

In previous studies we and others have demonstrated that cultured spindle cells derived from KS lesions of AIDS patients (AIDS-KS cells) produce factors inducing autocrine and paracrine chemotactic and growth effects for cells composing the KS lesions. Nakamura et al. *Science* 242:426 (1988); Salahuddin *Science* 242:430 (1988); Ensoli et al. *Science* 243:223 (1989); Ensoli et al. *Hematol. Oncol. Clin. North Am.* 5:281 (1991); Ensoli et al. *Immunol. Rev.* 127:147 (1992); Roth et al. Oncogene 4:483 (1989); Miles et al. *Proc. Natl. Acad. Sci. USA* 89:4068 (1990); Sturzl *Proc. Natl. Acad. Sci. USA* 89:7046 (1992); Thompson et al. *Cancer Res.* 54:2670 (1991).

Supernatants from AIDS-KS cells induce normalsendothelial cells to proliferate, degrade and cross the basement membrane, followed by migration and organization into tube-like structures. Ensoli et al. *Science* 243:223 (1989); Ensoli et al. *Hematol. Oncol. Clin. North Am.* 5:281 (1991); Ensoli et al. *Immunol. Rev.* 127:147 (1992); Thompson et al. *Cancer Res.* 54:2670 (1991). These are the same events that are required for the formation of new blood vessels or angiogenesis. Folkman et al. *Nature* 288:551 (1980); Folkman et al. *Science* 235:442 (1987). In fact, we have also reported that when AIDS-KS cells are placed into the chorioallantoic membrane of 9 day-old fertilized chick eggs they induce the formation of new blood vessels. Further, when KS-cells are injected into nude mice they induced vascular lesions of mouse cell origin resembling human KS. Salahuddin, et al. *Science* 242:430 (1988).

Molecular analysis of the factors produced by AIDS-KS cells revealed that several factors were produced, including: interleukin-1α (IL-1α), IL-1β, endothelial cell growth factor (ECGF), granulocyte-monocyte colony stimulating factor (GM-CSF), transforming growth factor-β (TGF-β), platelet derived growth factor (PDGF), IL-6, IL-8, and basic fibroblast growth factor (bFGF). bFGF, IL-1β, IL-6, and IL-8, however, are produced in relatively higher quantities than the others. In particular, high steady state levels of mRNA encoding bFGF, a potent angiogenic factor, are expressed by the cells and released into the extracellular media in a biologically active form. Ensoli et al. *Science* 243:223 (1989); Ensoli et al. *Hematol. Oncol. Clin. North Am.* 5:281 (1991); Ensoli et al. *Immunol. Rev.* 127:147 (1992); Burgress et al. *Annu. Rev. Biochem.* 58:575 (1989). AIDS-KS cells were found to contain abundant storage of different bFGF protein isoforms of 18, 23, and 25 kD with both nuclear and cytosolic distribution.

Measurements of the bFGF content and lactic dehydrogenase activity in supernatants of AIDS-KS cells confirmed that bFGF release was directly related to the abundance of intracellular bFGF molecules. By using specific antibodies directed against bFGF we found that this cytokine induces the growth of AIDS-KS cells, normal endothelial cells, and other mesenchymal-derived cells (B. Ensoli, *Science* 243:223 (1983). Therefore, bFGF acts as both an autocrine (tumor cell specific) and paracrine (normal cell specific) growth factor. Ensoli et al. *Science* 243:223 (1989); Ensoli et al. *Hematol. Oncol. Clin. North Am.* 5:281 (1991); Ensoli et al. *Immunol. Rev.* 127:147 (1992).

As endothelial cell growth is the event required for angiogenesis and antibodies against bFGF blocked endothelial cell growth stimulated by AIDS-KS cells, this suggested that bFGF was responsible for angiogenesis in KS. B. Ensoli, *Science* 243:223 (1989). bFGF was also reported to be overexpressed in vivo, by spindle cells in human KS lesions from both AIDS-associated and classical KS. Xerri et al. *Am. J. Pathol.* 138:9 (1991).

A great deal of time, money, and effort has been invested in strategies to block the proliferative effects of cellular growth factors. Major resources have been invested into strategies for making antisense oligonucleotides to such growth factors in an effort to block their proliferative activities. In one experiment in vitro Kaposi's sarcoma cells were treated with antisense oligonucleotides against the cytokine IL-6. See Miles et al. *Proc. Nat. Acad. Sci. USA* 87:4068–4072 (1990) (embodied in International Patent Application No.: PCT/US92/04509, Publication No.: WO 92/21380 (the "Miles Application")). In the references, IL-6 was suggested to be the autocrine factor primarily responsible for proliferation of Kaposi's sarcoma cells. See Miles Application at p. 4, lines 29–33. However, IL-6 has not been shown to possess the angiogenic properties necessary for the full proliferation of Kaposi's sarcoma. Moreover, the reference indicates that relatively high dosages of antisense oligonucleotides are necessary to block the IL-6 induced proliferation of Kaposi's sarcoma. Miles Application at p. 4, lines 17–22.

Accordingly, it would be advantageous to determine the factors primarily responsible for the histogenesis (or development) of Kaposi's sarcoma and to provide methods of blocking their proliferative and angiogenic effects in vivo.

SUMMARY OF THE INVENTION

In one aspect of the present invention, there is provided a method of inhibiting the progression of Kaposi's sarcoma in a patient. This method comprises administering to the patient an effective Kaposi's sarcoma progression-inhibiting amount of an antisense oligonucleotide having binding affinity for RNA encoding basic fibroblast growth factor. Examples of useful antisense oligonucleotide for this purpose are oligonucleotides having SEQ ID NO:1, SEQ ID NO:2, or SEQ ID NO:3. Each of these sequence ID numbers are defined hereinbelow.

Another aspect of the present invention relates to a method to monitor the progress of Kaposi's sarcoma in a patient. This method includes the steps of: (a) isolating a first sample of a bodily fluid containing a detectable quantity of basic fibroblast growth factor from a patient having Kaposi's sarcoma at a first time, (b) measuring the amount of basic fibroblast growth factor in the first sample, (c) isolating a second sample of the bodily fluid from the patient at a second time later than the first time, and (d) measuring the amount of basic fibroblast growth factor in the second sample. A decrease in the amount of basic fibroblast growth factor measured in step (d) in comparison to the amount measured in step (b) indicates a remission in the Kaposi's sarcoma. In a preferred embodiment, an increase in the amount of basic fibroblast growth factor measured in step (d) in comparison to the amount measured in step (b) indicates a worsening in the Kaposi's sarcoma. The method can be used to monitor the progress of a treatment of Kaposi's sarcoma using an agent having therapeutic effect on Kaposi's sarcoma in a patient. When so used the method additionally comprises administering the agent having therapeutic effect on Kaposi's sarcoma to the patient between the first and second times.

Still another aspect of the present invention is a pharmaceutical preparation for use in the treatment of Kaposi's sarcoma. This composition includes an antisense oligonucleotide having binding affinity for RNA encoding basic fibroblast growth factor. Examples of useful antisense oligonucleotide sequences in this composition include oligonucleotides having a sequence of SEQ ID NO:1, SEQ ID NO:2, or SEQ ID NO:3.

DETAILED DESCRIPTION OF THE PREFERRED EMBODIMENTS

We have discovered that basic fibroblast growth factor (bFGF) has a pinnacle role in the proliferation and angiogenic activity of AIDS-Kaposi's sarcoma cells. Unexpectedly, antisense oligonucleotides having homology with bFGF RNA can almost totally abrogate the proliferation and angiogenic activity of KS cells. This result was unexpected in light of the great number of growth related factors produced by cultured AIDS-KS cells (i.e., IL-1β, IL-6, IL-8, and bFGF) and the general unpredictability of performing antisense experiments in vivo. Previously it had been postulated that IL-6 was the primary activator of KS cell proliferation. See Miles et al. supra; Miles Application supra.

The bFGF antisense phosphothioate oligodeoxynucleotides were exceptionally effective in blocking KS cell growth and angiogenic activity. They showed an in vitro KS cell antiproliferative effect of approximately 10 times the control in which no blocking of growth was observed. Further, the dose required to obtain the antiproliferative effect was relatively low, i.e., 0.5 $\mu$M–1.0 $\mu$M to block cell proliferation, as compared to the optimal dosage taught in the Miles Application (15–20 $\mu$M for IL-6). This provides an advantage in that less antisense bFGF oligonucleotides will be necessary for treating KS in comparison to antisense molecules against other cytokines, such as IL-6. Even more unexpected, the bFGF antisense oligonucleotides were effective in blocking the angiogenic activity of AIDS-KS cells.

Growth Stimulation by Cytokines of KS

We and others have demonstrated the ability of a variety of cytokines to promote or stimulate the growth of AIDS-KS cells. An example of this work is provided below.

EXPERIMENT I

Cytokine Stimulation of AIDS-KS Cells

AIDS-KS cell growth can be stimulated by cytokines present in conditioned medium from activated T cells (HTLV II CM or activated primary T cells), as described by Nakamura et al. *Science* 242:426 (1988) and Barillari et al. *J Immunol.* 149:3727 (1992), the disclosures of which are hereby incorporated by reference. Two cultures of AIDS-KS cells were established and cultured as described in Nakamura et al. *Science* 242:426 (1988) and Barillari et al. *J Immunol.* 149:3727 (1992). Both cultures were trypsinized and plated for cell growth assays as described previously (Ensoli *Science* 243:223 (1989); Barillari et al. *J Immunol.* 149:3727 (1992)) then various quantities of IL-1α, IL-1β, TNFα, TNFβ, IL-6, and oncostatin were added to the cells. The cell growth was measured by the cell count 5–6 days following inoculation with the respective cytokine or through a tritiated thymidine incorporation assay at 48 hours as described in Ensoli et al. *J. Virol.* 67:277 (1993), the disclosure of which is hereby incorporated by reference. The results of this experiment are shown in Table 1.

TABLE 1

| SAMPLE | % Cell Growth by Cell County After 5–6 Days | % Cell Growth by by 3[H] Tymidine Incorporation at 4 p.m |
|---|---|---|
| IL-1 α 1 ng/mL | 25% | 70% |
| 10 | 75% | 100% |
| 50 | 50% | 142% |
| IL-1 β 1 ng/mL | 25% | 50% |
| 10 | 50% | 100% |
| 50 | 50% | 75% |
| TNF α 1 ng/mL | 45% | 84% |
| 10 | 100% | 120% |

TABLE 1-continued

| SAMPLE | % Cell Growth by Cell County After 5–6 Days | % Cell Growth by by 3[H] Tymidine Incorporation at 4 p.m |
|---|---|---|
| 50 | 30% | 63% |
| TNF β 1 ng/mL | 25% | 50% |
| 10 | 80% | 74% |
| 50 | 100% | 74% |
| IL-6 1 ng/mL | 0% | ND |
| 10 | 25% | ND |
| 50 | 25% | 30% |
| ONCOSTATIN 1:10,000 M | 100% | 128% |

The results presented in Table 1 as measured by cell counts are also found in Barillary et al. *J. Immun.* 149:3727–3236 (1992), the disclosure of which is hereby incorporated by reference. It will be seen from the results in Table 1 that a variety of cytokines have a growth proliferative effect on the AIDS-KS cells. The growth proliferative effect, however, occurs irrespective of the cytokines ability to promote angiogenesis.

As discussed above, recent data obtained through measuring the bFGF content and lactic dehydrogenase activity in the supernatants of AIDS-KS cells confirmed that bFGF release was directly related to the abundance of the intracellular bFGF molecules. By using specific antibodies directed against bFGF we have shown that bFGF released by AIDS-KS cells induces the growth of AIDS-KS cells themselves, normal endothelial cells, and other mesenchymal derived cells.

This data suggested that bFGF itself was able to induce, at least partially, the histological changes found in nude mice by transplanted AIDS-KS cells as well as those found in human KS lesions. To verify this hypothesis, we performed experiments wherein increasing amounts of bFGF were injected subcutaneously into nude mice. AIDS-KS cells were used as a positive control, while normal endothelial cells derived from human umbilical vein (h-UVE cells), bovine serum albumin (BSA), and the buffer or media in which the proteins or cells were resuspended were used as negative controls. The mice were sacrificed at 6–7 days post-injection. These results and the experimental protocol are detailed below.

TABLE 2

|  | Lesion* | Angiogenesis # | Spindle Cells # | Acute Inflammation # | Chronic Inflammation # | Edema # |
|---|---|---|---|---|---|---|
| bFGF 0.1 μg | 0/8 | 25% (2) | 63% (2) | 50% (2) | 60% (2) | 60% (2) |
| 1 μg | 7/20 | 90% (3) | 100% (4) | 60% (2) | 60% (3) | 60% (3) |
| 10 μg | 11/11 | 100% (6) | 100% (6) | 70% (2) | 100% (3) | 100% (3) |
| 30 μg | 19/19 | 100% (7) | 100% (7) | 100% (2) | 100% (3) | 100% (3) |
| 90 μg | 10/10 | 100% (8) | 100% (8) | 100% (2) | 100% (3) | 100% (3) |
| BSA 90 μg | 0/2 | 0% | 0% | 0% | 0% | 0% |
| Buffer | 0/36 | 0% | 19% (1) | 25% (1) | 19% (1) | 25% (1) |
| AIDS-KS Cells $3 \times 10^6$ | 10/10 | 100% (5) | 100% (5) | 100% (7) | 100% (5) | 100% (4) |
| H-UVE Cells $3 \times 10^6$ | 0/6 | 0% | 0% | 0% | 0% | 0% |

*Number of mice developing vascular lesions versus number of mice inoculated. # percentage of mice inoculated developing histological alterations. In parenthesis is reported the "intensity" value for each histopathological feature observed (see legend).

The results presented in Table 2 were derived through the following procedure.

EXPERIMENT II

Role of bFGF as Principal Factor in Kaposi's Sarcoma

In this experiment, bFGF (Boheringer-Manheim) (0.1 to 90 μg as shown in Table 2), BSA (Sigma) (90 μg), AIDS-KS cells, or H-UVE cells ($3 \times 10^6$) were injected subcutaneously into the lower back (right side) of BALB/c nu/nu athymic mice. In addition, negative controls consisting of buffer or media in which the proteins or the cells were resuspended, respectively, were injected into the left side of the same mice. In all cases, the protein or the cells in 200 μl were mixed with 200 μl of Matrigel (Collaborative Research) (Thompson et al. *Cancer Res.* 54:2670 (1991)) prior to injection. Matrigel is a mixture of basement membrane components which, in the presence of angiogenic factors, facilitates the formation of site-specific vessels. Thompson et al. *Science* 241:1349 (1988).

Six to seven days following injection with either the proteins or the cells, the mice were sacrificed. At this time, the sites of injection were evaluated macroscopically for the presence of vascular lesions.

The size of the lesions ranged from 4×5 mm to 9×12 mm and developed within 3–4 days, reaching maximum size by day 6–7. Tissue samples were taken from both sites of the animals and fixed in formalin. Slides were prepared from the tissue blocks, coded, and analyzed microscopically after hematoxylin-eosin (H & E) staining. The evaluation was performed "blindly." The values were graded according to the intensity of the histological changes observed at the site of injection: blood vessel formation, spindle cell formation and proliferation, acute (neutrophilic) and chronic (mononuclear) inflammatory cell infiltration and edema.

These histopathological features were evaluated in comparison with the negative controls and was given a unit value (intensity value). For angiogenesis, which was always absent in the negative controls, the minimal alteration observed was given a value of 2. Vascular lesions and histological changes were also observed in the absence of matrigel, however, higher bFGF concentrations or AIDS-KS cells numbers were necessary to induce lesions. In addition, lesions were smaller and less delimited than in the presence of matrigel.

Macroscopically, bFGF induced vascular lesions at the site of injection with a frequency related to the dose inoculated. (Table 1). The lesions were indistinguishable from the lesions induced by the AIDS-KS cells and both developed within 3–4 days, reaching maximum size by day 6–7. Histologically, the lesions induced by bFGF were very similar to those induced by AIDS-KS cells and both presented alterations closely resembling human KS, such as, angiogenesis, spindle cell formation and proliferation. The percentage of mice developing these histopathological features and the intensity of the alterations were dependent on the dose of the bFGF inoculated. (Table 1). Further, acute (neutrophilic) and chronic (mononuclear) inflammatory cell infiltration and edema were present in bFGF-induced lesions, however, they were more pronounced and/or evident in cells inoculated with AIDS-KS cells (Table 2). This is in agreement with data indicating that the AIDS-KS cells, in addition to producing bFGF, also produce other cytokines that mediate inflammatory effects, such as IL-1, IL-8, and vascular permeability factor.

In contrast, BSA and H-UVE inoculated cells did not show any signs of histological alteration. However, the buffer in which bFGF was resuspended in a few cases (7–9 out of 36) induced some minor histological alterations. These latter minor alterations may have, in fact, been due to the injection procedure itself and detectable since more mice were inoculated with the control buffer.

These results are consistent with previous observations indicating that bFGF induces histological features also present in KS lesions such as spindle cell formation (Weindel et al. *Biochem. Biophys. Res. Comm.* 183:1167 (1992)) and KS spindle cell proliferation and angiogenesis (Ensoli et al. *Science* 243:223 (1989). Further, bFGF was expressed in high levels in vitro and in vivo by the spindle cells of human KS lesions. Ensoli et al. *Science* 243:223 (1989). Taken together, we speculated that the bFGF cytokine could play a key role in KS histogenesis.

ANTIPROLIFERATIVE AND ANTIANGIOGENIC EFFECTS OF bFGF ANTISENSE OLIGOMERS

Because bFGF appears to play a significant role in KS development and progression, we decided to determine if an antisense sequence against bFGF RNA would be effective in inhibiting AIDS-KS cell growth and audiogenic activity, and, ultimately, arrest the progression of KS in vivo. In connection therewith, we turned to the use of antisense oligodeoxynucleotides directed to a nucleotide sequence of the bFGF RNA. For a particularly valuable review of the design considerations and use of antisense oligonucleotides, see Uhlmann et al. *Chemical Reviews* 90:543–584 (1990) the disclosure of which is hereby incorporated by reference.

While in principle oligonucleotides having a sequence complementary to any region of the bFGF gene find utility in the present invention, oligodeoxynucleotides complementary to a portion of the bFGF mRNA transcript including the translation initiation codon are particularly preferred. Also preferred are oligonucleotides complementary to a portion of the bFGF mRNA transcript lying within about 40 nucleotides upstream (the 5' direction) or about 40 nucleotides downstream (the 3' direction) from the translation initiation codon.

As used herein, and unless otherwise indicated, the term "oligonucleotide" includes strands of either ribonucleotides or deoxyribonucleotides.

The term "oligonucleotide" and "oligodeoxynucleotide" include not only oligomers and polymers of the common biologically significant nucleotides, i.e., the nucleotides adenine ("A"), deoxyadenine ("dA"), guanine ("G"), deoxyguanine ("dG"), cytosine ("C"), deoxycytosine ("dC"), thymine ("T") and uracil ("U"), but also include oligomers and polymers hybridizable to the bFGF mRNA transcript which may contain other nucleotides. Likewise, the terms "oligonucleotides" and "oligodeoxynucleotides" may include oligomers and polymers wherein one or more purine or pyrimidine moieties, sugar moieties or internucleotide linkages is chemically modified. The term "oligonucleotide" is thus understood to also include oligomers which may properly be designated as "oligonucleotides" because of modification of the internucleotide phosphodiester bond. Such modified oligonucleotides include, for example, the alkylphosphonate oligonucleosides, discussed below.

The term "phosphorothioate oligonucleotides" is defined as an oligonucleotide wherein one more of the internucleotide linkages is a phosphorothioate group, as opposed to the common phosphodiester group which is characteristic of unmodified oligonucleotides.

An "alkylphosphonate oligonucleoside" is defined as an oligonucleotide wherein one or more of the internucleotide linkages is an alkylphosphonate group, where R is an alkyl group preferably methyl or ethyl.

The term "bFGF mRNA transcript" is defined herein as the mRNA transcript encoding the bFGF protein. It will be understood that a variety of methods for determining the level of a gene's expression are well-known to those skilled in the art. Such methods include, for example, reverse transcriptase polymerase chain reaction (RT-PCR) analysis.

The full sequence of the bFGF gene is known. See Abraham et al. *Science* 233, 545 (1986), the disclosure of which is hereby incorporated by reference.

The antisense oligonucleotides of the present invention may be synthesized by any of the known chemical oligonucleotide synthesis methods. Such methods are generally described, for example, in Winnacker *From Genes to Clones: Introduction to Gene Technology*, VCH Verlagsgesellschaft mhH (H. Ibelgaufts trans. 1987).

Any of the known methods of oligonucleotide synthesis may be utilized in preparing the instant antisense oligonucleotides.

The antisense oligonucleotides are most advantageously prepared by utilizing any of the commercially available, automated nucleic acid synthesizers. One such device, the Applied Biosystems 380B DNA Synthesizer, utilizes β-cyanoethyl phosphoramidite chemistry.

Since the complete nucleotide synthesis of DNA complementary to the bFGF mRNA transcript is known, antisense oligonucleotides hybridizable with any portion of the bFGF transcript may be prepared by oligonucleotide synthesis methods known to those skilled in the art.

While any length oligonucleotide may be utilized in the practice of the invention, sequences shorter than 12 bases may be less specific in hybridizing to the target bFGF mRNA, may be more easily destroyed by enzymatic digestion, and may be destabilized by enzymatic digestion. Hence, oligonucleotides having 12 or more nucleotides are preferred.

Long sequences, particularly sequences longer than about 40 nucleotides, may be somewhat less effective in inhibiting bFGF translation because of decreased uptake by the target cell. Thus, oligomers of 12–40 nucleotides are preferred, more preferably 15–30 nucleotides, most preferably 18–26 nucleotides. Sequences of 18–24 nucleotides are most particularly preferred.

Oligonucleotides complementary to and hybridizable with any portion of the bFGF mRNA transcript can, in principle, effective for inhibiting translation of the transcript, and capable of inducing the effects herein described. It appears that translation is most effectively inhibited by blocking the mRNA at a site at or near the initiation codon. Thus, oligonucleotides complementary to the 5'-terminal region of the bFGF mRNA transcript are preferred. It is believed that secondary or tertiary structure which might interfere with hybridization is minimal in this region. Moreover, it has been suggested that sequences that are too distant in the 3'-direction from the initiation site may be less effective in hybridizing the mRNA transcripts because of a "read-through" phenomenon whereby the ribosome is postulated to unravel the antisense/sense duplex to permit translation of the message. See, e.g., Shakin, *J. Biochemistry* 261:16018 (1986).

The antisense oligonucleotide can additionally be directed to a site at or near one of the two splice donor-acceptor sites, i.e., splice donor-acceptor site 1 (codon 60) or splice donor-acceptor site 2 (codon 94-95).

While antisense oligomers complementary to one of the two splice donor-acceptor sites of the bFGF transcript are preferred, particularly the region including the first splice donor-acceptor site, it should be appreciated that useful antisense oligomers are not limited to those complementaryto the sequences found in the translated portion of the mRNA transcript, but also includes oligomers complementary to nucleotide sequences including the initiation codon, or contained in, or extending into, the 5'- and 3'-untranslated regions.

The following 24-mer oligodeoxynucleotide is complementary to the bFGF mRNA transcript beginning with the initiation codon of the transcript and extending downstream thereof (in the 5' direction):

5' GATGCTCCCGGCTGCCATGGTCCC 3' (SEQ ID NO:1).

Smaller oligomers based upon the above sequence, in particular, oligomers hybridizable to segments of the bFGF message containing the initiation codon, are also anticipated to be effective in blocking bFGF translation.

Also preferred is a 24-mer oligodeoxynucleotide is complementary to the bFGF mRNA transcript beginning with the splice donor-acceptor site 1 (codon 60) having the following sequence:

5' TTGTAGCTTGATGTGAGGGTCGCT 3' (SEQ ID NO:2).

The oligonucleotide employed may represent an unmodified oligonucleotide or an oligonucleotide analog. Thus, oligonucleotides hybridizable to the bFGF mRNA transcript finding utility according to the present invention include not only oligomers of the biologically significant native nucleotides, i.e., A, dA, G, DG, C, dC, T and U, but also oligonucleotide species which have been modified for improved stability and/or lipid solubility. For example, it is known that enhanced lipid solubility and/or resistance to nuclease digestion results by substituting an alkyl or alkoxy group for a phosphate oxygen in the internucleotide phosphodiester linkage to form an alkylphosphonate oligonucleotide or alkylphosphotriester oligonucleotide.

The phosphorothioates, in particular, are stable to nuclease cleavage and soluble in lipid. They may be synthesized by known automatic synthesis methods. Non-ionic oligonucleotides such as these are characterized by increased resistance to nuclease hydrolysis and/or increased cellular uptake, while retaining the ability to form stable complexes with coinplementary nucleic acid sequences. The alkylphosphonates in particular, are stable to nuclease cleavage and soluble in lipid. The preparation of alkylphosphonate oligonucleotides is disclosed in U.S. Pat. No. 4,469, 863. The methylphosphonates, in particular, are preferred. Methylphosphonate oligomers can be prepared by a variety of methods, both in solution and on insoluble polymer supports (Agrawal et al. *Nucl. Acids Res.* 6:3009–3024 (1979))

The most efficient procedure for preparation of methylphosphonate oligonucleotides involves use of 5'-Q-dimethoxytrityldeoxynucleoside-3'-Q-diisopropylmethylphosphoramidite intermediates, which are similar to the methoxy or β-cyanoethyl phosphoramidite reagents used to prepare oligodeoxyribonucleotides. The methylphosphonate oligomers can be prepared on controlled pore glass polymer supports using an automated DNA synthesizer (Sarin et al. *Proc. Natl. Acad. Sci. USA* 85:7448–7451 (1988).

Resistance to nuclease digestion may also be achieved by modifying the internucleotide linkage at both the 5' and 3' termini with phosphoroamidites according to the procedure of Dagle et al. *Nucl. Acids Res.* 18:4751–4757 (1990). Suitable nucleotide analogs for preparation of the antisense oligonucleotides described herein include but are not limited to the ethyl or methyl phosphonate analogs disclosed in U.S. Pat. No. 4,469,863.

Phosphorothioate oligonucleotides contain a sulfur-for-oxygen substitution in the internucleotide phosphodiester bond. Phosphorothioate oligonucleotides combine the properties of effective hybridization for duplex formation with substantial nuclease resistance, while retaining the water solubility of a charged phosphate analogue. The charge is believed to confer the property of cellular uptake via a receptor (Loke et al. *Proc. Natl. Acad. Sci. USA* 86:3474–3478 (1989)).

Phosphorothioate modified oligodeoxynucleotide are described by LaPlanche et al. *Nucleic Acids Research* 14:9081 (1986) and by Stec et al. *J. Am. Chem. Soc.* 106:6077 (1984). The general synthetic method for phosphorothioate oligonucleotides was modified by Stein et al. *Nucl. Acids Res.* 16:3209–3221 (1988), so that these compounds may readily be synthesized on an automatic synthesizer using the phosphoramidite approach. Also, additional modifications have been added by Zon et al. Zon et al. *Anti-Cancer Drug Design* 6:539–568 (1991); Zon et al. *Oliaonucleotides and Analogues: A Practical Approach*, F. Eckstein, Ed. (Oxford University Press, Oxford, England), pp. 87–108 (1991). See also Stec et al. U.S. Pat. No. 5,151,510.

Furthermore, recent advances in the production of oligoribonucleotide analogues mean that other agents may also be used for the purposes described here, e.g., 2'-O-methylribonucleotides (Inove et al. *Nucleic Acids Res.* 15:6131 (1987) and chimeric oligonucleotides that are composite RNA-DNA analogues (Inove et al. *FEBS Lett.* 215:327 (1987).

While inhibition of bFGF mRNA translation is possible utilizing either antisense oligoribonucleotides or oligodeoxyribonucleotides, free oligoribonucleotides are more susceptible to enzymatic attack by ribonucleases than oligodeoxyribonucleotides. Hence, oligodeoxyribonucleotides are preferred because, upon hybridization with bFGF mRNA, the resulting DNA-RNA hybrid duplex is a substrate for RNase H, which specifically attacks the RNA portion of DNA-RNA hybrid. Degradation of the mRNA strand of the duplex releases the antisense oligodeoxynucleotide strand for hybridization with additional bFGF messages.

In general, the antisense oligonucleotides of the present invention will comprise a sequence which is completely complementary to the target portion of the bFGF message. Absolute complementarity is not however required, particularly in larger oligomers. Thus, reference herein to a "nucleotide sequence complementary to at least a portion of the mRNA transcript" of bFGF does not necessarily mean a sequence having 100% complementarity with the transcript. In general, any oligonucleotides having sufficient complementarity to form a stable duplex with bFGF mRNA is suitable.

Stable duplex formation depends on the sequence and length of the hybridizing oligonucleotide and the degree of complementarity with the target region of the bFGF message. Generally, the larger the hybridizing oligomer, the more mismatches may be tolerated. One skilled in the art may readily determine the degree of mismatching which may be tolerated between any given antisense oligomer and the target bFGF message sequence, based upon the melting point, and therefore the stability, of the resulting duplex. Melting points of duplexes of a given base pair composition can be readily determined from standard texts, such as *Molecular Cloning: A Laboratory Manual* (2nd edition, 1989), J. Sambrook et al, Eds.

While oligonucleotides capable of stable hybridization with any region of the bFGF message are within the scope of the present invention, oligonucleotides complementary to a region including the first splice donor-acceptor site are believed particularly effective. Particularly preferred are oligonucleotides hybridizable to a region of the bFGF mRNA up to 24 nucleotides upstream (in the 5' direction) of codon 60.

Figure 2:
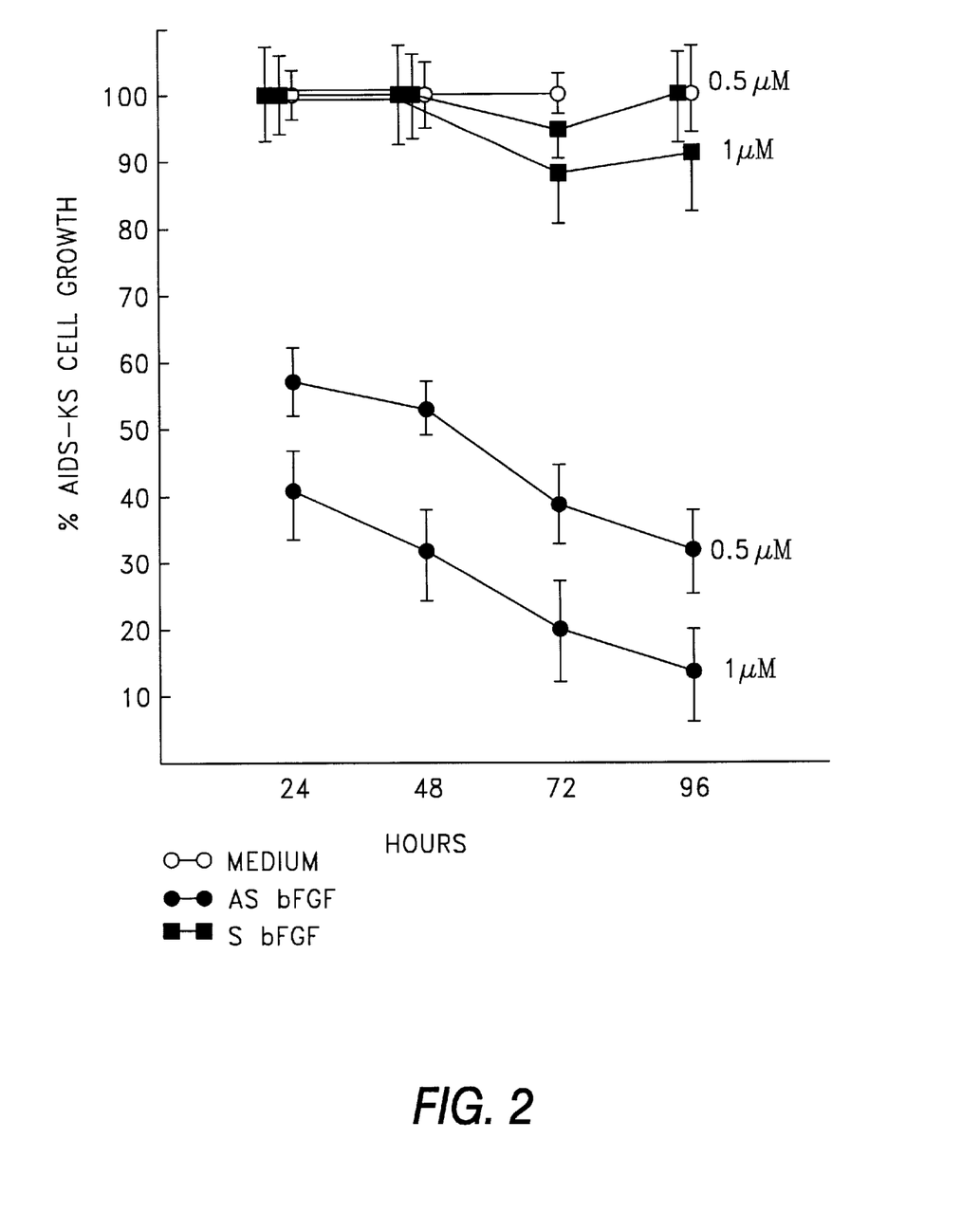
FIG. 2 is a line graph showing the time and dose dependent relationship of AIDS-KS cell growth in the presence of sense basic fibroblast growth factor (square) and antisense basic fibroblast growth factor (solid circle) phosphothioate oligodeoxynucleotides, with AIDS-KS cell growth in pure medium (hollow circle) as a control.

Accordingly, we synthesized phosphorothioate antisense oligodeoxynucleotides (24-mers) complementary to different portions of the bFGF mRNA sequence as described in Becker et al. *EMBO J.* 8:3685 (1989) in order to assay AIDS-KS cell growth or to block the angiogenic promoting activity produced by AIDS-KS cells (endothelial cell growth, migration, and invasion through basement membrane). The antisense oligomers chosen were complementary to the translation start site (AUG codon), the splice donor-acceptor site 1 (codon 60), and the splice donor-acceptor site 2 (codon 94-95) of the bFGF mRNA (FIG. 2A). Corresponding sense oligomers were used as controls.

EXPERIMENT III

Preparation of Antisense Oligonucleotides

Antisense and sense bFGF phosphorothioate oligodeoxynucleotides were prepared on 1 μmol or 10 μmol scales with an Applied Biosystems Model 380B DNA synthesizer using reported procedures in Zon et al. *Oligonucleotides and Analogues: A Practical Approach*, F. Eckstein, Ed. (Oxford University Press, Oxford, England), pp. 87–108 (1991), the disclosure of which is hereby incorporated by reference, which included substitution of a sulfur-donor reagent (as described in U.S. Pat. No. 5,151,510, the disclosure of which is hereby incorporated by reference) for iodine-water-pyridine, reversing the normal oxidation-then-cap sequence within each cycle, preparative reversed-phase high-performance liquid chromatography, detritylation, isolation of the final product in the form of its sodium salt, and then analysis by capillary gel electrophoresis. See also Zon et al. *Anti-Cancer Drua Design* 6:539 (1991), the disclosure of which is hereby incorporated by reference. Product was recovered as greater than or equal to 85 percent of full-length product through comparison to size standards.

The particular sequences of the AS oligomers were synthesized as follows. The antisense sequence complementary to the translation start site (AUG codon) of bFGF mRNA was:

5' GATGCTCCCGGCTGCCATGGTCCC 3' (SEQ ID NO:1).

The sequence of the antisense splice donor-acceptor site 1 (codon 60) was:

5'-TTGTAGCTTGATGTGAGGGTCGCT 3' (SEQ ID NO:2).

The sequence of the antisense splice donor-acceptor site 2 (codon 94-95) was:

5' ATCCGTAACACATTTAGAAGCCAG 3' (SEQ ID NO:3).

Corresponding sense oligomers were synthesized as controls, and had the following sequences:

5' GGGACCATGGCAGCCGGGAGCATC 3' (SEQ ID NO:4)

5' AGCGACCCTCACATCAAGCTACAA 3' (SEQ ID NO:5)

5' CTGGCTTCTAAATGTGTTACGGAT 3' (SEQ ID NO:6)

Following preparation of the antisense oligomers, we inoculated AIDS-KS cells with the oligomers to determine the extent of their antiproliferative effect.

EXPERIMENT IV

Inoculation of Cells with the bFGF Antisense Oligomers

After preparation, the oligomers were resuspended in sterile and endotoxin-free water at the concentration of 1 mM. Further dilutions were made in cell growth media. Cells were grown as described in Nakamura et al. *Science* 242:426 (1988); Ensoli et al. *J. Virol.* 67:277 (1993).

Figure 1:
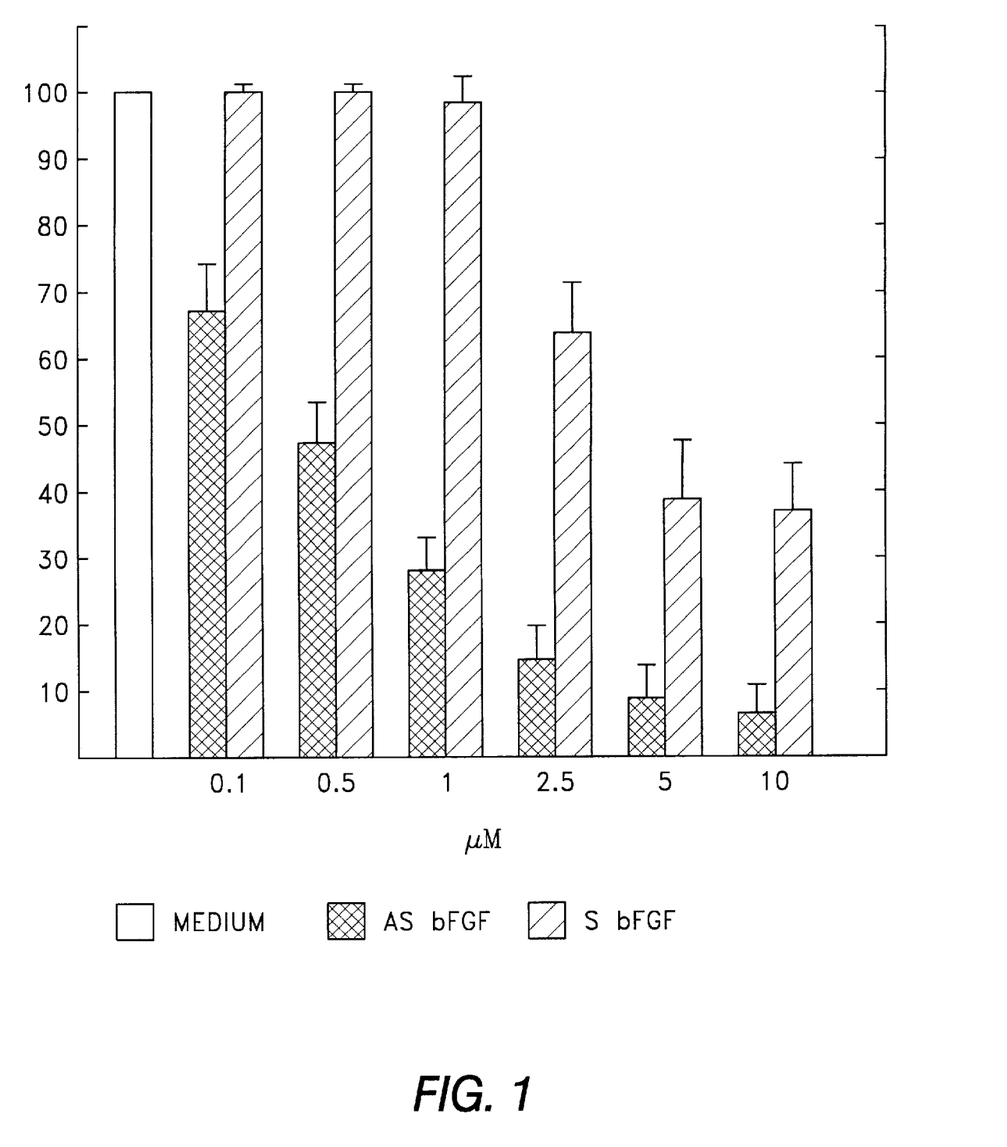
FIG. 1 is a bar graph showing the dose dependent relationship on AIDS-KS cell growth in the presence of sense basic fibroblast growth factor (hatched bar) and antisense basic fibroblast growth factor (solid bar) phosphothioate oligodeoxynucleotides, with AIDS-KS cell growth in pure medium (hollow bar) as a control.

In FIG. 1, it can be seen that the antisense oligomer directed against the first splice donor-acceptor site of bFGF mRNA corresponding to SEQ ID NO:2 inhibits AIDS-KS cell growth specifically and in a dose-dependent fashion. The percentage of AIDS-KS4 cell growth in the presence of medium alone (hollow bar), or in medium containing increasing concentrations (0.1–10 µM) of the antisense (AS) bFGF (■) or the sense (S) bFGF (hatched bar) oligomers is shown. AIDS-KS4 cells were established and cultured as described above. Cell growth was evaluated by $^3$[H]-thymidine incorporation assay (described above in Experiment I) at 48 hours after the addition of the oligomers to complete media (containing 10% FCS) and in the absence of any cell growth supplement. The results with the oligomers are expressed as the percentage of cell growth compared to results in the absence of the oligomers (% of controls). Similar or identical cell growth inhibitory effects were obtained with four different preparations of the same oligomers and with unmodified oligomers.

Since the AS oligomer directed against the first splice donor-acceptor site of bFGF mRNA corresponding to SEQ ID NO:2 inhibited the growth of AIDS-KS cells with higher activity and specificity compared to the other AS oligomers (data not shown), it was chosen for further experiments. The phosphothioate oligodeoxynucleotide antisense sequence directed against the first splice donor-acceptor site of bFGF mRNA corresponding to SEQ ID NO:2 will be referred to herein as AS bFGF. AS bFGF inhibited the growth of AIDS-KS cells in a dose-dependent fashion (FIG. 1).

In terms of specificity, optimal inhibitory effects were observed at 1 µM concentration of AS bFGF. At this concentration the AS bFGF oligomer inhibited more than 70% of AIDS-KS cell growth while the sense oligomer (S bFGF) had no significant effect (FIG. 1). Oligomer concentrations greater than 2.5 µM had some nonspecific effects as indicated by the presence of a certain degree of cell growth inhibition with the S oligomer.

To determine whether this was due to the phosphorothioate modification, unmodified oligomers were synthesized and used in similar experiments. The inhibition of AIDS-KS cell growth was similar or identical to that of the modified oligomers indicating that, at the concentration utilized, the phosphorothioate modification does not contribute to the inhibition of cell growth, while it has the advantage of increasing the half-life of these compounds.

Inhibition of AIDS-KS cell proliferation lasted for more than 96 hours after a single addition of the AS oligomer as shown in FIG. 2. FIG. 2 illustrates the cell growth inhibitory effect of AS bFGF over time after a single addition to AIDS-KS cells. Percentage of AIDS-KS4 cell growth at 24, 48, 72 and 96 hours after the addition to the cells of medium alone (hollow bar), or medium containing 0.5 or 1 uM of AS bFGF (solid bar) or S bFGF (hatched bar). Cell growth was evaluated as described in connection with FIG. 1.

Moreover, the effect of AS bFGF increased with time and at 96 hours 0.5 and 1 uM of the oligomer reached up to 68% and 86% of cell growth inhibition, respectively, while the S oligomer had no significant effects (FIG. 2). Since bFGF stimulates the G0-G1>S transition of the cell cycle (Fiorelli et al., in preparation), this result may be explained by the fact that a greater proportion of the cells entered the cell cycle over time and in the absence of bFGF cells are arrested in G0-G1, and/or by the fact that the intracellular storage of bFGF must be depleted before full inhibitory effects by AS are evident.

EXAMPLE V

Comparative Example of AIDS-KS Cell Growth Inhibition With Antisense bFGF Oligideoxynucleotides We have also compared the inhibition of AIDS-KS cell growth stimulated with cytokines present in conditioned media (CM) from activated T cells by AS bFGF to several other cytokines. The results are presented in the following Table, which shows the results from our $^3$[H]Thymidine incorporation assay, conducted as described above in Experiment I.

TABLE 3

| Cytokine | Oligomer µM | % of Cell Growth |
|---|---|---|
| IL-1 α 10 ng/ml | — | 100% |
| | Antisense 0.5 | 36% |
| | Sense 0.5 | 66% |
| Il-1 β 10 ng/ml | — | 100% |
| | Antisense 0.5 | 32% |
| | Sense 0.5 | 93% |
| TNF α 10 ng/ml | — | 100% |
| | Antisense 0.5 | 36% |
| | Sense 0.5 | 73% |
| TNF β 10 ng/ml | — | 100% |
| | Antisense 0.5 | 35% |
| | Sense 0.5 | 76% |
| ONCOSTATIN M 1:10,000 | — | 100% |
| | Antisense 0.5 | 42% |
| | Sense 0.5 | 81% |

IL-6 in our assay did not stimulate cell growth more than 25–30%, thus, it was not used for these experiments. See also Barillari et al. *J Immunol.* 149:3727 (1992). These results show that bFGF antisense oligomers inhibit AIDS-KS cell growth and proliferation (see below).

EXPERIMENT VI

Antisense bFGF Blocks The Activity of Other AIDS-KS Cell Growth Promoters and Inhibits AIDS-KS Cell Derived from Different Patients But Not Normal Endothelial Cells We also tested the ability of AS bFGF to block the growth promoting activity of other cytokines in addition to the antiproliferative effect of AS bFGF on other AIDS-KS cell lines. Experiments were performed as described in Experiment IV with the exception that cells were stimulated with conditioned media (1:5 to 1:8 dilutions) from activated T cell conditioned media.

Intriguingly, AS bFGF blocked AIDS-KS cell proliferation induced by known growth inducers of these cells such as conditioned media (CM) from activated T cells. CM contains several cytokines promoting AIDS-KS cell growth such as interleukin-1 (IL-1), tumor necrosis factor, IL-6 and the newly discovered AIDS-KS cell growth factor Oncostatin M. The effect of each of these cytokines is blocked by AS bFGF as shown in Example V.

This, and the fact that some of these cytokines are known to induce bFGF expression in vascular cells, suggest that bFGF acts as the final mediator of AIDS-KS cell growth. The indications that bFGF is the final mediator in the AIDS-KS pathway, provide our method with substantial advantages over others that are attempting to block cytokine related KS growth. By using antisense molecules against the final mediator in the cytokine cascade, our method can be effective for treating virtually all Kaposi's Sarcomas, no matter how they are stimulated. Antisense molecules against other cytokines may not be effective in treating all types of compounds that induce Kaposi's Sarcoma formation.

Figure 3:
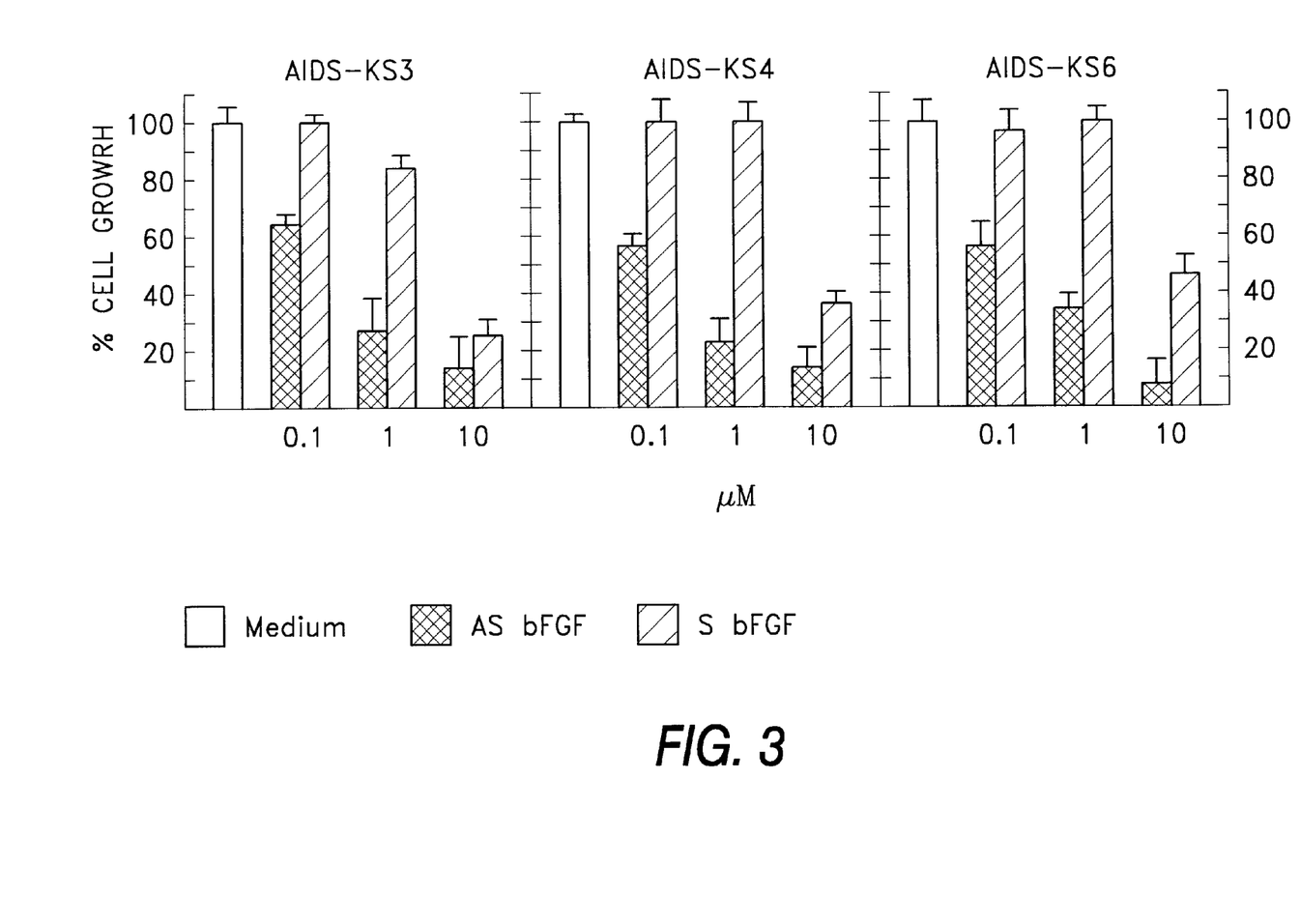
FIG. 3 is a bar graph showing the dose dependent relationship on AIDS-KS3, KS4, and KS6 cell growth in the presence of sense basic fibroblast growth factor (hatched bar) and antisense basic fibroblast growth factor (solid bar) phosphothioate oligodeoxynucleotides, with AIDS-KS cell growth in pure medium (hollow bar) as a control.

AS bFGF inhibited the growth of AIDS-KS cells derived from different patients (AIDS-KS3, -KS4 and -KS6). See FIG. 3 wherein the antisense bFGF oligomer inhibition of the growth of AIDS-KS cell cultures derived from different patients is shown. The percentage of AIDS-KS3, KS4 and KS6 cell growth 24 hours after the addition to the cells of medium alone (hollow bar) or medium containing 0.1, 1, and 10 $\mu$M of the AS bFGF oligomer as indicated by (■) or the S bFGF (hatched bar). In FIG. 3, clear inhibition is observed in these other cell lines.

Figure 4:
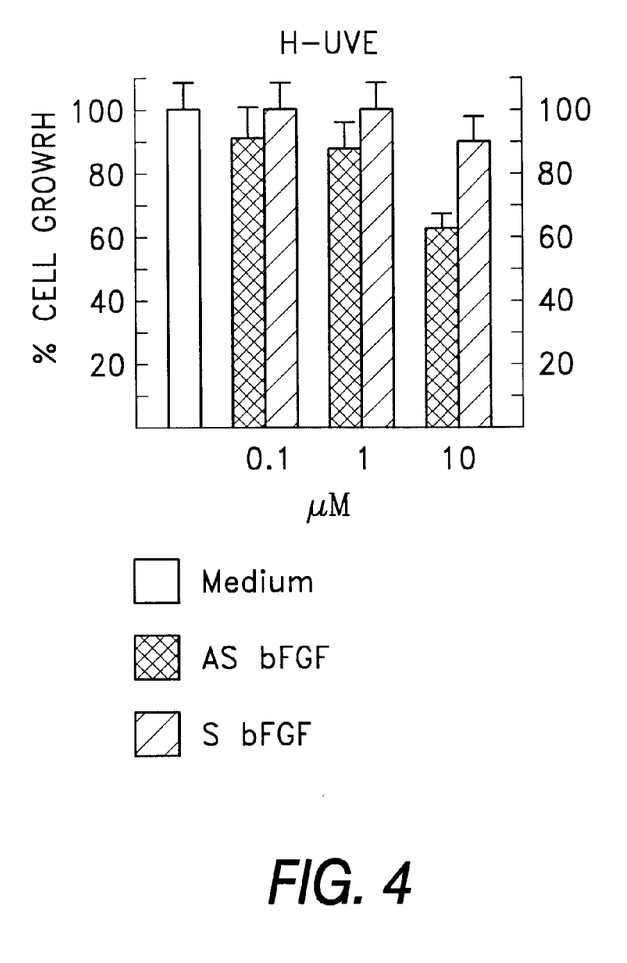
FIG. 4 is a bar graph showing the minimal effects of the presence of sense basic fibroblast growth factor (hatched bar) and antisense basic fibroblast growth factor (solid bar) phosphothioate oligodeoxynucleotides, on human umbilical vein cells (H-UVE), with H-UVE cell growth in growth medium (hollow bar) as a control.

However, there is no inhibition of normal endothelial cells (H-UVE cells), as shown in FIG. 4. This is important because it shows specificity and, possibly, lack of toxicity of AS bFGF in vivo (therapy). In FIG. 4 the percentage of H-UVE cell growth in the presence of medium (□) or in medium containing 0.1, 1, and 10 $\mu$M of the AS bFGF (■) or the S bFGF ( ) oligomers is shown. H-UVE cells were established and cultured in the presence of endothelial cell growth supplement (ECGS, 30 ug/ml, from Collaborative Research) or acidic FGF (10 ng/ml, from R and D or Bohering-Manheim) and heparin (45 ug/ml, from Sigma), as previously described. E.g., Ensoli et al. *Science* 243:223 (1989); Barillari et al. *J Immunol.* 149:3727 (1992). $^3$[H]-thymidine incorporation was evaluated 48 hours after the addition of the oligomers to complete media (containing 10% of FCS and ECG or aFGF), as previously described. Id.

Endothelial cells were chosen as the control cell type because they normally produce little or no bFGF, but respond by proliferating to the cytokine and because they may represent the cell type of origin of AIDS-KS cells.

These results indicate that the AS bFGF oligomer has specific growth inhibitory activity for cells producing high levels of bFGF and proliferating in response to the molecule, such as AIDS-KS cells.

EXPERIMENT VII

Immunoperoxidase Staining of AIDS-KS Cells with Affinity Purified anti-bFGF Monoclonal To verify whether the cell growth inhibition by AS bFGF was associated with a reduction of bFGF protein production, AIDS-KS cells were treated for 24 h with the AS or S bFGF (0.5 $\mu$M) or medium alone and then stained by double-indirect immunoperoxidase with affinity purified anti-bFGF monoclonal antibodies (Promega) (as in VII). Cells were analyzed for bFGF protein expression by double indirect immunoperoxidase method with anti-bFGF purified mouse monoclonal antibodies (1:150 dilution) raised against purified bovine brain bFGF (Promega), as described in Ensoli et al. *J. Virol.* 67:277 (1993).

After AS bFGF-treatment, the number of bFGF positive cells and the intensity of both the cytoplasmic and nuclear staining were greatly reduced compared to S bFGF-treated or untreated cells.

We observed that the antisense bFGF oligomer inhibits bFGF protein expression by AIDS-KS cells. AIDS-KS4 cells were cultured for 24 hours in medium alone, in the presence of AS bFGF or S bFGF (0.5 uM). Staining was reduced in the medium treated cells. The nuclear bFGF staining was also reduced in antisense treated cells (from 36%±9 to 3%±1 positive cells). SK-HEP1 cell line, a known bFGF producer cell line was used as a positive control (84%±5 bFGF positive cells). While a T cell line (H9) was used as a negative control (0%).

These results indicate that the AS oligomer specifically inhibited the expression of bFGF protein isoforms with both nuclear and cytosolic localization (15). This could be due to the degradation of the bFGF RNA/antisense complex by RNase H, as suggested in previous work with phosphorothioate oligomers (19).

EXPERIMENT VII

Blocking of the Angiogenic Activity of AIDS-KS Cells by Antisense bFGF Oligomers From the foregoing, it will be appreciated that AIDS-KS cells release biologically active bFGF into the cell culture supernatants in the absence of cell death. Moreover, conditioned medium from AIDS-KS cells induce endothelial cells to migrate, to degrade and cross the basement membrane and to proliferate. All these events are required for angiogenesis, a typical feature of KS which is an angioprolific disease. These events are all induced by injection of bFGF into mice.

Further, antisense bFGF blocked the angiogenic and proliferative activity of AIDS-KS cells, as shown by experiments with conditioned medium prepared from AIDS-KS cells treated for 24 hours with the AS or the S bFGF oligomer or with medium alone and used to stimulate H-UVE cell growth and cell invasion through matrigel. The results of these experiments are shown in FIGS. 5A and 5B.

Figure 5A:
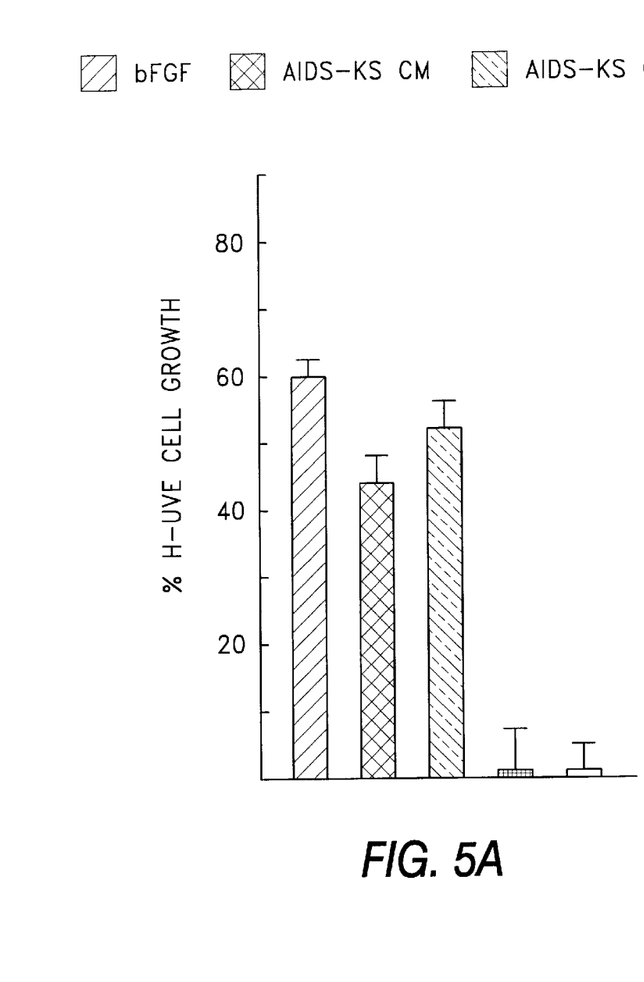
FIGS. 5A-5B are two bar graphs showing the effects on the growth (FIG. 5A) and invasion of H-UVE cells (FIG. 5B) of conditioned medium from AIDS-KS cells (crosshatched bar) cultured in the presence of an antisense phosphothioate oligodeoxynucleotide (AS bFGF/AIDS-KS CM) (solid bar), a sense phosphothioate oligodeoxynucleotide (S bFGF/AIDS-KS CM) (dotted bar), pure medium (AIDS-KS CM) (hollow bar), or basic fibroblast growth factor (bFGF) (hatched bar).
Figure 5B:
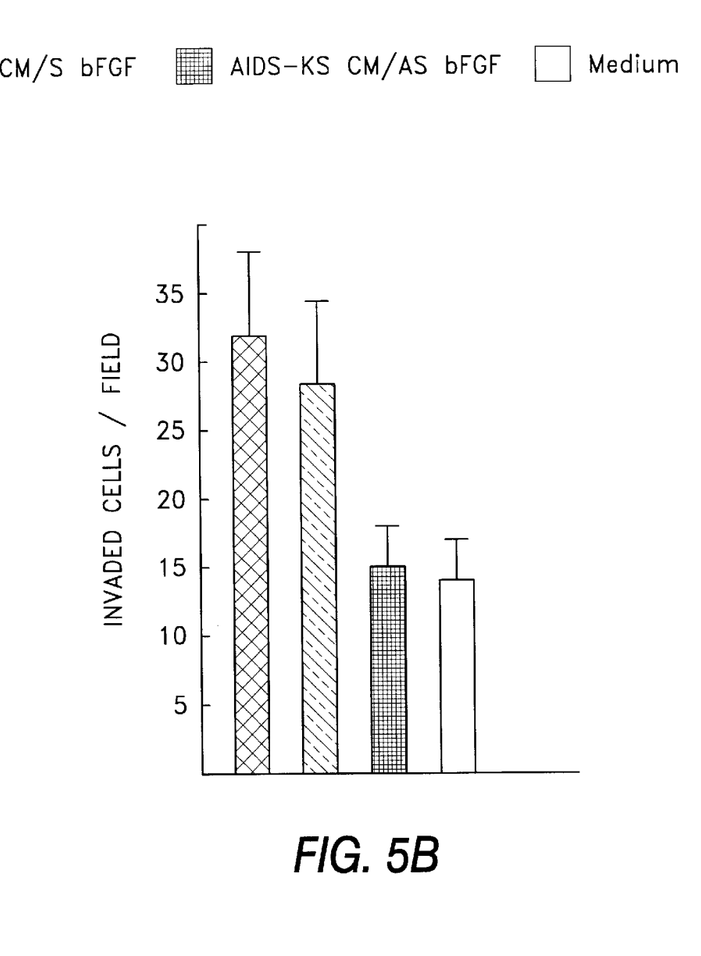

In FIGS. 5A and 5B, conditioned media from AIDS-KS cells treated with the antisense bFGF oligomer lose the ability to stimulate H-UVE cell growth (FIG. 5A) and the invasion of H-UVE cells through a reconstituted basement membrane (FIG. 5B). Matrigel is a reconstituted basement membrane used to evaluate the invasion potential of cells. Albini et al. *Cancer Res.* 47:3239 (1987).

FIG. 5A shows the percentage of H-UVE cell growth and FIG. 5B shows the number of invaded cells per field in the presence of bFGF (hatched bar), CM derived from AIDS-KS cells cultured in the absence of oligomers (AIDS-KS CM, cross-hatched bar), CM from AIDS-KS cells treated with the S bFGF oligomer (AIDS-KS CM/S bFGF, dotted bar), CM from AIDS-KS cells treated with the AS bFGF oligomer (AIDS-KS CM/AS bFGF, solid bar), or in the presence of medium alone (hollow bar). Conditioned medium was prepared as described in connection with Experiment IV from AIDS-KS4 cells treated for 24 hours with serum-free medium containing 0.5 $\mu$M of the AS or the S bFGF oligomers, or from untreated cells, from the same experiments described in FIG. 1. bFGF (5 ng/ml) and medium alone were used as positive and negative controls, respectively.

For the cell growth assays, conditioned medium was diluted 1:2 in growth media containing 20% fetal bovine serum (FBS) before the addition to H-UVE cells and cell growth evaluated by $^3$[H]-thymidine incorporation assays (48 hours) as previously described in Experiment I.

For the cell invasion assay, H-UVE cells (8×10$^4$) were resuspended in 800 ul of D'MEM/0.01% BSA and placed in the upper compartment of the Boyden chambers. In the lower compartment the conditioned medium or serum-free medium was placed. The two compartments of the Boyden chambers were separated by 12 M pore polycarbonate filters coated (50 $\mu$l/filter) with matrigel (diluted to a final concentration of 0.50 mg/ml) and the assay was performed as previously described. Albini et al. *Cancer Res.* 47:3239 (1987).

After incubation, the cells on the upper surface of the filters were removed, fixed in methanol and stained by H &

E. Invaded cells present on the lower surface of the filter were quantitated "blindly" by light microscopy. The assays were carried out in duplicate and 5 fields/filter were counted. The values reported are the average of 10 fields.

Conditioned medium from AIDS-KS cells treated with the AS oligomer did not induce the proliferation of endothelial cells nor did it induce these cells to migrate and to degrade and cross the basement membrane. On the contrary, conditioned medium from untreated cells or from cells treated with the S bFGF oligomer induced similar levels of H-UVE cell growth and invasion. This is consistent with recent data (in our laboratory) indicating that release of bFGF by AIDS-KS cells depends upon the abundance of the intracellular bFGF content which was reduced after AS treatment.

Our results indicate that AS oligomers targeting bFGF inhibit the growth and angiogenic effects of spindle cells derived from AIDS-KS lesions. Since bFGF is overexpressed in human KS lesions, and itself induces most of the histological features of KS. Therefore, we expect that bFGF is an optimal target for blocking KS development and progression. bFGF is present in KS lesions in both AIDS-associated and classical KS. Accordingly, we expect that therapies specifically directed to inhibit this molecule may be of benefit for all forms of KS.

Furthermore, these results are very promising since there is no indication that the AS bFGF oligomer cross-reacts or otherwise adversely affects the normal endothelial (H-UVE) cells. This indicates that the AS bFGF oligomer can be used in effective therapeutic procedures.

Preparation of Other Therapeutic Antisense Oligomers

It is also possible to prepare additional antisense oligomers in the expectation that one or more antisense oligomers to bFGF (other than SEQ ID NOS:1–3) will have superior antiproliferative effect.

The full sequence of the bFGF gene is known. See S. A. Abraham et al. *Science* 233, 545 (1986), the disclosure of which is hereby incorporated by reference. The preparation of additional antisense constructs is accordingly within easy reach of those of ordinary skill in the art. The basic techniques used in connection with Experiment III, and its introduction, are used.

The resulting antisense oligomers are then tested to determine if they are more effective in their antiproliferative activity than the antisense oligomers of SEQ ID NOS:1–3. Such testing preferably takes the form of the following experiment.

EXPERIMENT IX

Testing Antisense Oligomers for Enhanced Antiproliferative Effect

After synthesizing an antisense oligonucleotide sequence of the gene encoding for bFGF, the newly synthesized antisense oligomer is administered to a first group of cells from a mammal, at least a portion of said cells being Kaposi sarcoma cells. The rate of proliferation of the cells is measured. Thereafter, the rate of proliferation of the cells is compared to the rate of proliferation for a known antisense oligonucleotide sequence. If an improved antiproliferative effect or a decrease in proliferation of the cells is observed for the newly synthesized antisense oligomer, relative to the rate of proliferation for cells treated with the known antisense oligomers, a superior therapeutic agent for KS is expected.

For example, the known antisense oligonucleotide sequence can be any one of SEQ ID NOS:1–3. Most preferably, the oligodeoxynucleotide corresponding to SEQ ID NO:3.

In Vivo Treatment of KS With Antisense Oligomers

Although in vivo antisense therapy has only recently been performed (Bayever et al. *Antisense Research and Development* 2:109–110 (1992)) it is expected to become a very promising method of treating disease. The following experiments present methods for treating Kaposi's sarcoma in human patients using bFGF antisense oligonucleotides.

The advantages of using AS bFGF oligomers in KS therapy compared to other approaches to date are several and include: (i) as discussed above, we have demonstrated several lines of evidence that indicate that bFGF is a key molecule involved in the development of KS lesions; (ii) the high specificity of antisense bFGF oligomers for the bFGF RNA molecule; (iii) the relative specificity of the antisense bFGF oligomers for AIDS-KS cells, and (iv) in vitro inhibition at low, non-toxic concentrations which are achievable in vivo, as shown by the results of animal studies with phosphorothioate oligomers directed to other targets.

Accordingly, we believe that KS therapy with antisense bFGF oligomers will be an efficacious form of therapy.

As will be understood, in order to effectively treat KS with the antisense oligomers of the present invention, it is necessary that the oligomers are able to gain access to the afflicted area. Moreover, it will be appreciated that any of the antisense oligomers prepared in accordance with the present invention that show antiproliferative effect can be used in treatment. However, preferably the antisense oligomer of SEQ ID NO:2 is used because of its proven effectiveness.

We expect that direct injection into lesions and intravenous administration of the antisense oligomers of the present invention are currently the most efficient and expedient forms of delivery. However, it is also anticipated that a variety of topical formulations will show similar efficacy. Intravenous administration is generally indicated in advanced cases of KS where the disease is usually generalized. For example, where a patient has more than 10 lesions, typically the KS is visceral. Moreover, where a patient has this number of lesions, they would be in extreme discomfort if each lesion was directly injected.

In either event, it is predictable, just as bFGF is taken up by cells in vivo, as demonstrated above in connection with Table 2 and Experiment 2, that the antisense oligonucleotides will behave similarly in vivo as they behaved in vitro.

Typically, the antisense oligomers of the present invention are formulated into a medicament to aid in stabilizing and/or aiding their delivery to the afflicted site. A multitude of appropriate formulations can be found in the formulary known to all pharmaceutical chemists: Remington's Pharmaceutical Sciences, 15th Edition, 1975. Mack Publishing Company, Easton, Pa. 18042. (Chapter 87:Blaug, Seymour).

For direct injection into lesions or in intravenous administration of the antisense oligomers it is conventional to include in the formulations physiologically acceptable buffers, excipients, and/or other delivery agents. For topical use, appropriate formulations include for example, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax. Topical application may be highly effective. For example, certain investigators have demonstrated that certain antisense oligomers are readily absorbed by the skin. In particular, these researcher used methylphosphonates. Uhlmann et al. *Chemical Reviews* 90:543–584 at p. 568 (1990).

Moreover, liposomes have shown great promise in assisting in the delivery of oligomers, in general, and antisense oligomers in particular. One highly advantageous example of a suitable liposomal delivery vehicle is prepared from cationic lipids, such as those available under the trademark LIPOFECTIN (Life Technologies, Inc., Bethesda, Md.).

The concentration or dose of the antisense oligomers of the present invention should range from 0.1 $\mu$M through 20 $\mu$M, depending on the seriousness of the affliction, or more preferably from 0.5 $\mu$M to 5 $\mu$M. The dosage will also depend on the type of oligonucleotide and also upon its chemical modification, if any. As will be understood, the schedule of the administration will also depend on the type of oligomers used and their chemical modification, since different chemical modification increase the half-life of these compounds.

EXPERIMENT X

Inhibition of KS Lesions Formation with AIDS-KS cells Pretreated with AS-bFGF

In order to determine if the AS bFGF was effective in halting the progression of KS in vivo, we will pretreat AIDS-KS cells with AS bFGF to attempt to block lesion formation. As discussed in connection with the Experiment described with Table 2, AIDS-KS cells when injected into mice will induce KS like lesions, Salahuddin et al., *Science*, supra (1988). Therefore we expect that we can block lesion formation from the AIDS-KS cells if pretreated with AS bFGF.

AIDS-KS cells are grown as described above. Cells are inoculated with varying quantities of AS bFGF or S bFGF, from 0.5 $\mu$M to 10 $\mu$M. After 2–3 days, aliquots of the cultures are withdrawn and injected (2–3 million cells per size) into athymic mice as previously described (Salahuddin et al., *Science* (1988)). The mice injected with AIDS-KS cells that was inoculated with AS bFGF do not form KS like lesions or form smaller lesions compared with mice injected with the untreated or S bFGF-treated AIDS-KS cells which form lesions.

EXPERIMENT XI

Induction of KS Lesions with AIDS-KS Followed by Direct Injection of AS-bFGF

KS like lesions were generated in athymic mice as described in Experiment__ (Table 2) with AIDS-KS cells (Salahuddin et al.). The mice are injected with AS-bFGF or S bFGF in phosphate buffered saline at concentrations ranging from 0 $\mu$M to 10 $\mu$M or 0 to 600 $\mu$g micrograms, directly into the lesions. In mice not injected with AS bFGF, their lesions continue to develop. However, in mice treated with AS bFGF, have smaller lesions or lesions do not develop.

EXPERIMENT XII

Induction of KS Lesions with AIDS-KS Followed by Intravenous Administration of AS-bFGF KS like lesions were generated in athymic mice as described in Experiment__ (Table 2) with AIDS-KS cells. The mice are injected intravenously with AS-bFGF or S bFGF in phosphate buffered saline at concentrations such to achieve serum concentrations of 0.1 to 10 $\mu$M. In mice not injected with AS bFGF, their lesions continue to develop. However, in mice treated with AS bFGF, their lesions are smaller or do not develop.

EXPERIMENT XIII

In Vivo Treatment of KS With Direct Injection

A patient having HIV associated KS in a relatively early stage is treated by direct injection of the antisense oligomer of SEQ ID NO:2 in a physiologically compatible buffer. The patient has approximately 10 lesions. The dosing is begun on day 1 with an initial injection of the equivalent of about 0.5–1 $\mu$M into each lesion. Dosing is continued every 3–4 days over a period of 1–3 weeks. Thirty days after the initiation of treatment, the size of the lesions have decreased. After 60 days, normal coloration of the skin should return where the lesions once were. If not a second cycle of treatment is performed.

EXPERIMENT XIV

In Vivo Treatment of KS With Intravenous Administration

A patient having HIV associated KS in a relatively advanced stage is treated by intravenous administration of the antisense oligomer of SEQ ID NO:2 in a physiologically compatible buffer. The patient has approximately 25 skin lesions and visceral lesions. The dosing is begun on day 1 with an initial intravenous administration of the equivalent to achieve serum levels of 0.1–1 $\mu$M. Dosing is continued every 3–4 days over a period of 1–3 weeks. Thirty days after the initiation of treatment, the size of the lesions have decreased. After 60 days, normal coloration of the skin returns where the lesions once were. If no, a second cycle of treatment is performed.

Combination Therapies With Antisense Oligomers

Recent drug based therapies have been proposed for the treatment of KS and some are currently in clinical trials, such as fumagillin and SP-PG (a proto glycan). Ingber et al. *Nature* 348:555 (1990); Nakamura et al. *Science* 255:1437 (1992). Both drugs have been shown to inhibit angiogenesis and to be effective in reducing the growth of tumors, including KS.

Combination therapies of AS bFGF with drugs inhibiting angiogenesis or tumor growth by different mechanisms is also viable for KS therapy, as recently proposed by Folkman and lngber for the association of fumagillin and $\alpha$-interferon in cancer therapy. Folkman et al. *Seminars in Cancer Biology* 3:89 (1992).

We have previously demonstrated that antibodies to bFGF are effective in reducing AIDS-KS cell growth and angiogenic effect. See Ensoli et al. *Science* 243:223 (1989). There, when conditioned medium from AIDS-KS cells was incubated with bFGF antisera, the induction of H-UVE cells was specifically blocked. AIDS-KS cell growth was similarly inhibited by bFGF antisera. Also, affinity-purified neutralizing antibodies to native bovine brain bFGF inhibited the growth of AIDS-KS cells.

Therefore, it is expected that bFGF antisense oligomer in connection with an antibody or antisera to bFGF will have efficacy in reducing the progression of KS in vivo. Angiogenesis is essential to the growth of many tumors and can be blocked by several drugs. However, compounds blocking specifically the production of angiogenic factors are lacking. Our data demonstrates that antisense oligonucleotides against angiogenic factors may have a broad application in cancer therapy.

The present invention has been described in connection with certain preferred embodiments. Such embodiments are exemplary rather than limiting. Accordingly, no matter how detailed the foregoing may appear in text, it will be understood that the true scope of the invention is governed only through a proper interpretation of the appended claims and any equivalents thereof.

What we claim is:

1. A method of inhibiting the proliferation of Kaposi's sarcoma cells in vivo, comprising contacting the cells with an effective Kaposi's sarcoma proliferation-inhibiting amount of an antisense oligonucleotide which is complementary to and hybridizes with RNA encoding basic fibroblast growth factor, said antisense oligonucleotide having the sequence of SEQ ID NO:2.

2. A pharmaceutical preparation useful for inhibiting the proliferation of Kaposi's sarcoma cells in vivo comprising an antisense oligonucleotide which is complementary to and hybridizes with RNA encoding basic fibroblast growth factor, said antisense oligonucleotide having the sequence of SEQ ID NO:2.

3. A reaction mixture comprising Kaposi's sarcoma (KS) cells and an antisense oligonucleotide which is complementary to and hybridizes with an mRNA encoding basic fibroblast growth factor, said antisense oligonucleotide having been selected by a process comprising the steps of:
   contacting a test sample of cultured AIDS-KS cells with an antisense oligonucleotide to produce a treated test sample; and contacting a control sample of cultured AIDS-KS cells with a control oligonucleotide to produce a treated control sample;

measuring the proliferation rate of cells in the treated test sample and in the treated control sample; and selecting said antisense oligonucleotide if the proliferation rate of AIDS-KS cells in the treated test sample is lower than the proliferation rate of AIDS-KS cells in the treated control sample.

4. The pharmaceutical composition of claim 3, wherein said control oligonucleotide is a sense oligonucleotide complementary to said antisense oligonucleotide.

5. The pharmaceutical composition of claim 3, wherein said control oligonucleotide is an antisense polynucleotide that is known to inhibit growth of AIDS-KS cells in vitro.

6. The pharmaceutical composition of claim 4, wherein said control oligonucleotide has the sequence of SEQ ID NO:5, and wherein said antisense oligonucleotide has the sequence of SEQ ID NO:2.

7. The pharmaceutical composition of claim 5, wherein said antisense polynucleotide has the sequence of SEQ ID NO:2.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: double
       (D) TOPOLOGY: linear    (ii) MOLECULE TYPE: cDNA   (iii) HYPOTHETICAL: NO    (iv) ANTI-SENSE: NO     (v) FRAGMENT TYPE:

(vi) ORIGINAL SOURCE:

(xi) SEQUENCE DESCRIPTION: SEQ ID NO:1:

GATGCTCCCG GCTGCCATGG TCCC                                    24

(2) INFORMATION FOR SEQ ID NO:2:

(i) SEQUENCE CHARACTERISTICS:
       (A) LENGTH: 24 base pairs
       (B) TYPE: nucleic acid
       (C) STRANDEDNESS: double
       (D) TOPOLOGY: linear    (ii) MOLECULE TYPE: cDNA   (iii) HYPOTHETICAL: NO    (iv) ANTI-SENSE: NO     (v) FRAGMENT TYPE:

(vi) ORIGINAL SOURCE:

(xi) SEQUENCE DESCRIPTION: SEQ ID NO:2:

TTGTAGCTTG ATGTGAGGGT CGCT                                    24

(2) INFORMATION FOR SEQ ID NO:3:

(i) SEQUENCE CHARACTERISTICS:
       (A) LENGTH: 24 base pairs
       (B) TYPE: nucleic acid
       (C) STRANDEDNESS: double
       (D) TOPOLOGY: linear    (ii) MOLECULE TYPE: cDNA   (iii) HYPOTHETICAL: NO    (iv) ANTI-SENSE: NO     (v) FRAGMENT TYPE:

(vi) ORIGINAL SOURCE:

(xi) SEQUENCE DESCRIPTION: SEQ ID NO:3:

ATCCGTAACA CATTTAGAAG CCAG                                    24

(2) INFORMATION FOR SEQ ID NO:4:

(i) SEQUENCE CHARACTERISTICS:

-continued (A) LENGTH: 24 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

GGGACCATGG CAGCCGGGAG CATC                                      24

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

AGCGACCCTC ACATCAAGCT ACAA                                      24

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

CTGCGTTCTA AATGTGTTAC GGAT                                      24